(12) United States Patent
Tsuchiya et al.

(10) Patent No.: US 7,382,531 B2
(45) Date of Patent: Jun. 3, 2008

(54) MICROSCOPE AND METHOD OF PREVENTING DEW CONDENSATION ON OBJECTIVE LENS

(75) Inventors: Atsuhiro Tsuchiya, Tokyo (JP); Katsuyoshi Yamaguchi, Tokyo (JP); Akitsugu Kagayama, Tokyo (JP); Kazuhiro Hasegawa, Tokyo (JP); Hideaki Endo, Tokyo (JP); Kenichi Koyama, Kanagawa (JP)

(73) Assignee: Olympus Corporation, Tokyo (JP)

( * ) Notice: Subject to any disclaimer, the term of this patent is extended or adjusted under 35 U.S.C. 154(b) by 54 days.

(21) Appl. No.: 11/259,392

(22) Filed: Oct. 26, 2005

(65) Prior Publication Data

US 2006/0092506 A1    May 4, 2006

(30) Foreign Application Priority Data

Oct. 28, 2004   (JP)   ............................. 2004-314253

(51) Int. Cl.
*G02B 21/26* (2006.01)

(52) U.S. Cl. ...................................... 359/395; 359/398

(58) Field of Classification Search ........ 359/392–395, 359/398

See application file for complete search history.

(56) References Cited

U.S. PATENT DOCUMENTS

| 4,629,862 A | 12/1986 | Kitagawa et al. |
| 5,343,018 A | 8/1994 | Limbach |
| 5,552,321 A | 9/1996 | Focht |
| 6,493,135 B1 | 12/2002 | Engelhardt |
| 2005/0105172 A1* | 5/2005 | Hasagawa et al. .......... 359/368 |

FOREIGN PATENT DOCUMENTS

| DE | 731 829 C | 2/1943 |
| DE | 202 14 480 U1 | 1/2003 |
| JP | 7-36118 U | 7/1995 |
| JP | 2002-250869 A | 9/2002 |
| JP | 2004-141143 A | 5/2004 |
| SU | 809024 A1 | 2/1981 |
| WO | WO 03/014719 A1 | 2/2003 |

\* cited by examiner

*Primary Examiner*—Joshua L Pritchett
(74) *Attorney, Agent, or Firm*—Frishauf, Holtz, Goodman & Chick, P.C.

(57) ABSTRACT

The problem to be solved by the present invention is to provide a microscope that prevents a dew condensation on an objective lens and allows obtaining a good microscopic image, and a method of preventing a dew condensation on an objective lens.

A microscope includes an objective lens having a heater 22 in a cell incubator 3 having a high humidity space. The high humidity space is maintained at 90% to 100% of relative humidity and controlled to be at a predetermined gas temperature. A cultured cell 12 in the cell incubator 3 is observed via the objective lens 1, and the heater 22 is controlled to make the temperature of the objective lens 1 higher than the gas temperature of the high humidity space.

19 Claims, 6 Drawing Sheets

MICROSCOPE AND METHOD OF PREVENTING DEW CONDENSATION ON OBJECTIVE LENS

CROSS-REFERENCE TO RELATED APPLICATIONS

This application is based upon and claims the benefit of priority from Japanese Patent Application No. 2004-314253, filed Oct. 28, 2004; the entire contents of which are incorporated herein by reference.

BACKGROUND OF THE INVENTION

1. Field of the Invention

The present invention relates to a microscope employed for a cell incubator and a method of preventing dew condensation on an objective lens of such microscope.

2. Description of the Related Art

In a field of biology and the like, observations of behaviors of living cells of animals and plants, which are kept alive under an appropriate condition, are generally carried out for a functional analysis of a living organism.

A cell incubator is employed to keep the living cell alive under a constant environmental condition for the observation of behavior of the living cell.

One conventional technique for observing a cultured cell which can be kept alive in the cell incubator with a microscope is disclosed in Japanese Patent Application Laid-Open No. 2004-141143, entitled "Incubator for Observation with Microscope," in which the cell incubator is placed on a stage of an inverted microscope for observation.

According to this technique, a cell culture space in which the cell in the incubator is placed is controlled as to maintain a constant condition, i.e., constant temperature, humidity, and $CO_2$ concentration, for example, respectively at 37° C., 100%, and 5%. The cell is kept alive under such constant environmental condition inside the incubator and a time course thereof or the like is observed with the microscope.

Here, the space inside the incubator is not completely thermally insulated from outside air. For example, an objective lens is placed so that a lens barrel thereof is disposed at a side of outside air of the incubator, whereas a top lens is disposed in the vicinity of the cell inside the incubator.

If an objective lens with a short working distance (WD) is employed, a distance between a cover glass to which the cell is pasted and a surface of the top lens of the objective lens is approximately 0.1 to 0.2 millimeter (mm). When a general dry objective lens is employed, air is filled between the cover glass and the surface of the top lens. Hence, a certain effect of thermal insulation can be expected to be exerted. However, when an immersion objective lens is employed, water or oil is filled between the cover glass and the top lens, whereby the effect of thermal insulation is significantly degraded. More specifically, since the objective lens is exposed to the outside air merely via water or oil filled in a small space of approximately 0.1 to 0.2 mm, and the cover glass to which the cell is pasted is disposed relative to the objective lens, the cell is deprived of the heat by the objective lens via oil or water. Hence, especially when the temperature of the outside air is low, it is difficult to maintain the temperature of the cell at 37° C.

A technique to solve the above described problem is to add a heater for the objective lens, which is disclosed, for example, in Japanese Patent Application Laid-Open No. 2002-250869, entitled "Lens Heater and Heating Apparatus with Lens Heater for Microscopic Observation," in which the objective lens is warmed up by heat emitted from a nichrome wire, and in Japanese Utility Model Application Laid-Open No. H7-36118, entitled "Microscope," in which the immersion objective lens is warmed up to a predetermined temperature through a distribution of water of a predetermined temperature. Here, the cell is maintained at a predetermined temperature (37° C., for example), through the control of the heater which serves to warm up the cell culture space in the incubator, as well as the control of an objective lens heater which serves to warm up the objective lens.

The techniques as disclosed in the above cited documents have various problems.

Firstly, though the cell culture space of the incubator is maintained in an environment in the temperature of 37° C. and at 100% humidity, the temperature of the objective lens is approximately 20° C., i.e., room temperature. Hence, when the objective lens as such is brought closer to the cell for focusing, the temperature of the objective lens suddenly increases and is exposed to a highly humid environment. Due to the differential temperature here, dew is condensed on the surface of the top lens of the objective lens to cause mist. When the objective lens employed in the microscope has a high numerical aperture (NA), even a tiny amount of mist causes degradation of microscopic image, hampering a satisfactory observation. In addition, when the objective lens with a high NA and a short WD is employed in the inverted microscope, sometimes a hole is provided on a bottom surface of the incubator, since the incubator needs to be moved together with the cell on the stage to change a portion to be observed. With the structure as described above, however, the objective lens is subjected to an air in high temperature and high humidity leaked out from the cell culture space, and the top lens is easily misted. Further, since WD is short, the top lens is brought even closer to the highly humid cell, which is another reason for misting over of the top lens.

According to the techniques as disclosed in Japanese Patent Application Laid-Open No. 2002-250869 and Japanese Utility Model Application Laid-Open No. H7-36118, the dew condensation on the top lens is prevented through heating of the objective lens 1. In the apparatuses disclosed in Japanese Patent Application. Laid-Open No. 2002-250869, and Japanese Utility Model Laid-Open No. H7-36118, the temperature of the objective lens is controlled through heating so that the temperature of the cell is always maintained at 37° C. Though the temperature of the top lens of the objective lens is controlled to be close to 37° C., it may become lower than 37° C., for example, approximately 36.9° C. or lower, depending on the temperature inside the cell culture space of the incubator, the temperature outside, or the like. For example, the gas temperature of the cell culture space, the temperature of the cell, the temperature of the top lens of the objective lens, and the outside temperature may become stable, respectively, at 38° C., 37° C., 36° C., and 35° C.

Under such condition, since the humidity inside the cell culture space is 100%, when the temperature of the top lens is lower than the gas temperature inside the cell culture space even by 0.1° C., dew is sometimes condensed on an outer surface of the top lens, whereby the microscopic image taken by the objective lens is significantly degraded.

In general, in the objective lens, the top lens is fixed to a metal middle frame of the objective lens barrel via bonding or caulking, for example. Hence, when the top lens is exposed to the cell culture space with 100% humidity, water vapor inside the cell culture space may permeate through the bonded portion, or leaks out from a tiny gap of approximately a few μm in the caulked portion, whereby the leaked out water vapor is gradually accumulated inside the objective lens. When the internal temperature of the objective lens is substantially equal to the gas temperature of the cell culture space and approximately 37° C., inside of the objective lens gradually becomes 100% in humidity. If the temperature variation inside the objective lens is such that the temperature of some portion or location thereof is slightly lower than 37° C., dew condensation occurs at such portion. When dew is condensed on any of the lenses in the objective lens, the microscopic image is degraded similarly as described above hampering a satisfactory observation.

Further, the incubator is provided with a lid or a cover having a similar function to allow the observer to take out a case in which the cell is placed from the cell culture space, exchange, or supply a new case with a cell. When the lid or the door is opened/closed, the outside air of a low temperature may invade into the cell culture space. Then, the air touches the top lens of the objective lens to suddenly cool the objective lens, causing dew condensation from the water vapor accumulated inside the objective lens. Then, similarly as described above, the microscopic image is degraded and a satisfactory observation becomes unachievable.

SUMMARY OF THE INVENTION

A microscope according to one aspect of the present invention includes a high humidity space that is maintained at a predetermined gas temperature and a predetermined relative humidity for culture of a living sample; an objective lens having a tip portion with a top lens which is disposed in the high humidity space, and serving to allow for an observation of the living cell incubated inside the high humidity space; a heater that heats the objective lens; and a temperature controller that controls the heater so that a surface temperature and an internal temperature of the objective lens are higher than a dew-point temperature and lower than a thermal death point of the living sample.

A microscope according to another aspect of the present invention includes a high humidity space that is maintained in a predetermined gas temperature and a predetermined relative humidity for a culture of a living sample; an objective lens having a tip portion with a top lens that is disposed in the high humidity space and serving to allow for an observation of the living sample incubated inside the high humidity space; a heater that heats the objective lens; an opening/closing unit that opens the high humidity space to an outside space; an open/close detector that detects an open/close state of the opening/closing unit; and a temperature controller that controls the heater so that a surface temperature and an internal temperature of the objective lens are higher than a dew-point temperature and lower than a thermal death point of the living sample, and so that the heater performs a more rapid heating when the opening/closing unit is in the open state than a heating performed when the opening/closing unit is in the close state.

A method of preventing dew condensation on an objective lens according to still another aspect of the present invention includes controlling a heater that heats an objective lens having a tip portion with a top lens which is disposed in a high humidity space maintained in a predetermined gas temperature and a relative humidity of 90 to 100% for a culture of a living sample, the objective lens allowing for an observation of the living sample incubated in the high humidity space, so that a surface temperature and an internal temperature of the objective lens are higher than a dew-point temperature and lower than a thermal death point of the living sample.

DETAILED DESCRIPTION OF THE PREFERRED EMBODIMENTS

Exemplary embodiments of the present invention will be described in detail below with reference to the drawings.

Figure 1:
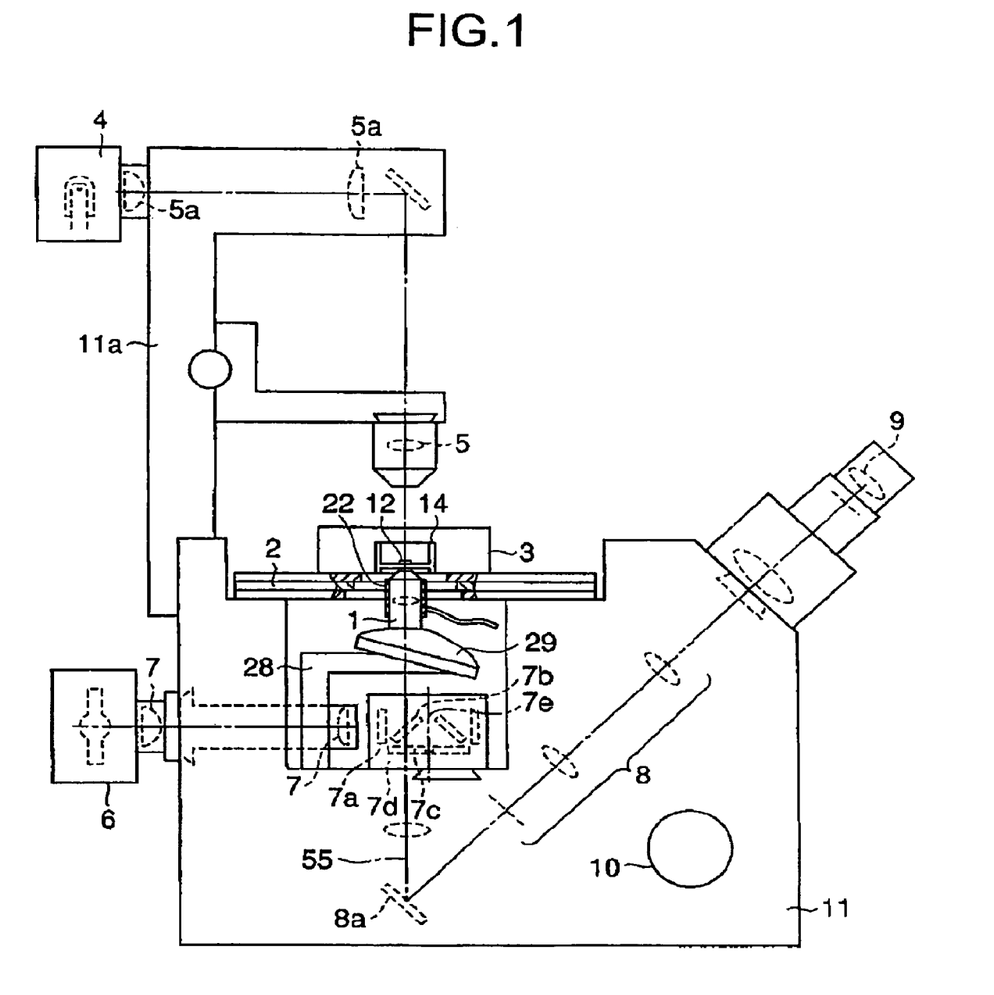
FIG. 1 is a schematic diagram of a structure of an inverted microscope according to a first embodiment of the present invention.

FIG. 1 shows a schematic structure of an inverted microscope according to a first embodiment of the present invention.

In FIG. 1, on a main microscope housing 11, a stage 2 is disposed. The stage 2 is horizontally movable along an X-Y direction according to a manipulation of a stage handle (not shown). On the stage 2, a cell incubator 3 containing a cultured cell 12, which is a living sample, is placed. The cell incubator 3 will be described in detail later.

The main microscope housing 11 has a lighting pillar 11a which faces down to the stage 2. The lighting pillar 11a has a top portion which extends in a substantially horizontal direction forming a substantially right angle with a surface of the stage 2.

The lighting pillar 11a has a light source 4 for transmissive lighting. The light source 4 may be a halogen lamp, a mercury lamp, or the like. A light beam emitted from the light source 4 passes through an optical path on which a transmissive lighting optical system 5a and a condenser 5 are arranged sequentially. The condenser 5 is disposed right above the cell incubator 3 on the stage 2 and serves to condense light from the light source 4 on the cultured cell 12.

Under the stage 2, an objective lens 1 is disposed. Plural objective lenses 1 of different magnifications are arranged and held by a revolver 29, though only one objective lens 1 is shown in FIG. 1. The revolver 29 is rotationally operable around a predetermined rotation axis as to switch the objective lens 1 disposed on an optical axis 55. The revolver 29 is secured to the main microscope housing 11 via an objective lens holder 28, and vertically movable along the optical axis 55 according to a manipulation of a focus handle 10 so that the observer can change a relative distance between the stage 2 and the objective lens 1 to properly focus the objective lens 1 on the cultured cell 12.

Under the revolver 29, a reflective mirror 8a is disposed on the optical axis 55. Light transmitting the cultured cell 12 is enlarged by the objective lens 1 and forms an image to be observed, which is deflected by the reflective mirror 8a in an obliquely upward direction (a direction forming an angle of 45 degrees with respect to the horizontal direction).

Then, the image deflected by the reflective mirror 8a is relayed through a relay optical system 8 and enters an eyepiece 9 which serves as an observation unit. Thus, the image is visually observable by the observer.

The microscope includes another light source 6 which is an incident lighting source formed with a halogen lamp, a mercury lamp, or the like. On an optical path formed by a light beam emitted from the light source 6, an incident lighting optical system 7, and a mirror unit cassette 7d structured like a turret are disposed. The mirror unit cassette 7d serves as an optical element switching unit. The mirror unit cassette 7d has an exciting filter 7a, a dichroic mirror 7b, an absorption filter 7c, and is rotatable around a rotation axis 7e. With a rotation around the rotation axis 7e, the exciting filter 7a, the dichroic mirror 7b, and the absorption filter 7c are disposed at a crossing point of the optical path from the light source 6 and the optical axis 55. FIG. 1 shows the mirror unit cassette 7d in such state. The mirror unit cassette 7d also has a hole (not shown).

When the inverted microscope with the above-described structure is employed for the observation with transmissive lighting, the hole (not shown) in the mirror unit cassette 7d is disposed on the optical path. Then, the emitted light from the light source 4 passes through the transmissive lighting optical system 5a and is focused on the cultured cell 12 via the condenser 5. Observation light passes through the cultured cell 12 is formed into an image by the objective lens 1, deflected by the reflective mirror 8a, passes through the relay optical system 8, and reaches the eyepiece 9 to be visually observed by the observer.

When a phase-contrast observation is performed, light through a ring slit (not shown) arranged in the transmissive lighting optical system 5a is projected on a phase film on the objective lens 1. On the other hand, if a differential interference contrast (DIC) observation is desired, a deflecting plate, a DIC prism, or the like are arranged in the transmissive lighting optical system 5a, and the relay optical system 8.

When a fluorescent observation is desired, the exciting filter 7a, the dichroic mirror 7b, and the absorption filter 7c are arranged on the optical path through the manipulation of the mirror unit cassette 7d. Then, light emitted from the light source 6 is condensed by the incident lighting optical system 7, and subjected to wavelength splitting by the exciting filter 7a so as to have an optimal exciting wavelength for a fluorescent dye applied to the cultured cell 12. Thereafter the light is reflected by the dichroic mirror 7b and passes through the objective lens 1 to be focused on the cultured cell 12. Fluorescence emitted from the cultured cell 12 passes through the objective lens 1 and the dichroic mirror 7b, and only components with a necessary fluorescent wavelength for observation is selected by the absorption filter 7c. The selected light is deflected by the reflective mirror 8a, passes through the relay optical system 8, and visually observed through the eyepiece 9.

Figure 2:
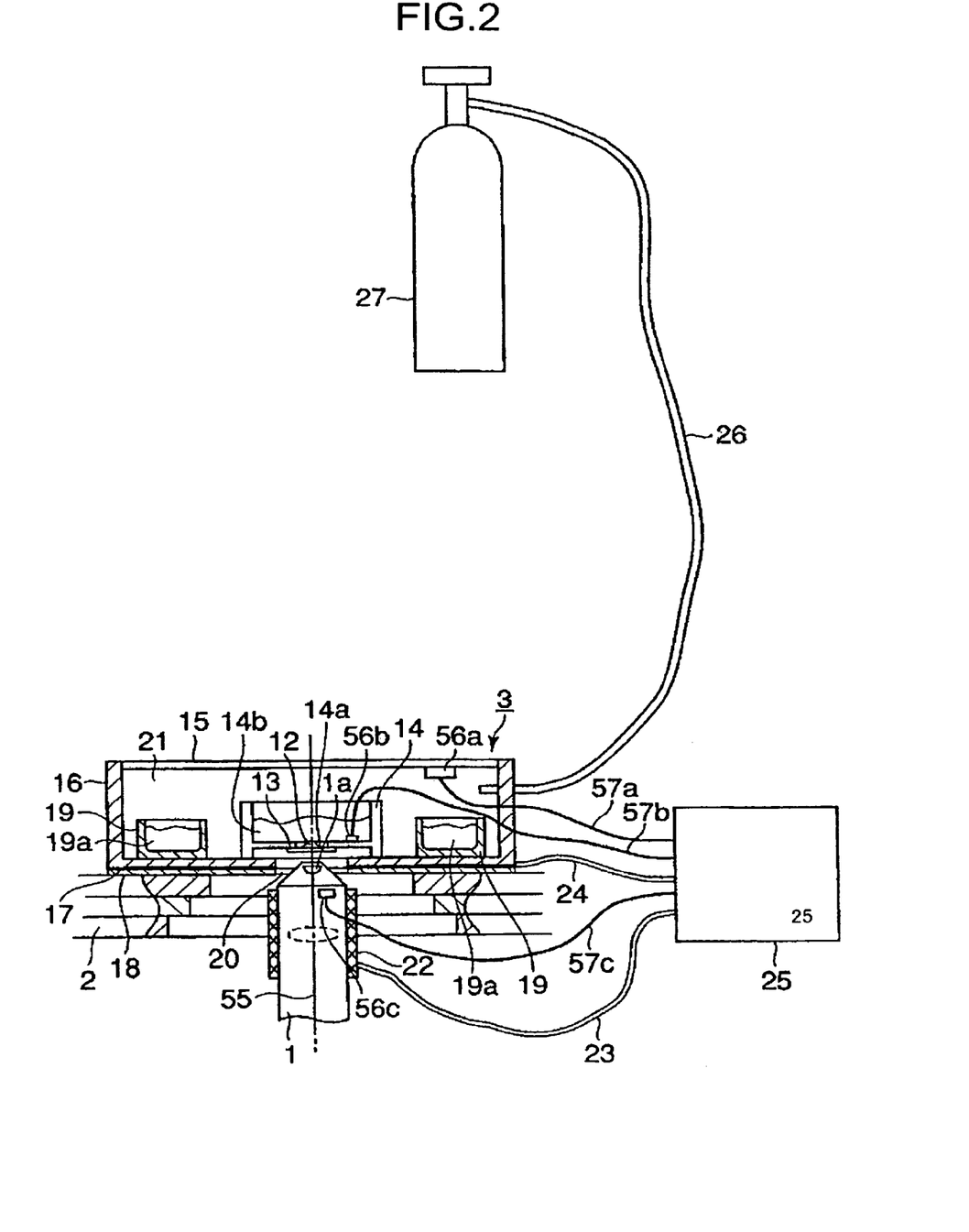
FIG. 2 is a schematic diagram of a structure of main parts including a cell incubator of the inverted microscope according to the first embodiment.

FIG. 2 shows a schematic structure of main parts including the cell incubator 3 in the microscope according to the first embodiment.

In FIG. 2, the cell incubator 3 includes a heat-retention box 16 which has an opening in a top portion, and a bottom surface is on the stage 2. On the bottom surface of the heat-retention box 16, a bottom plate 18 formed from a heat insulating member is provided to suppress heat transfer to the stage 2.

A transmission hole 20 provided on the bottom surface of the heat-retention box 16 penetrates the bottom plate 18. Through the transmission hole 20, a tip portion of the objective lens 1 having a top lens can be inserted. Thus, a focusing on the cultured cell 12 is possible even with the objective lens 1 with a high NA and a short WD. Here, the transmission hole 20 has such a diameter that an inner wall of the transmission hole 20 does not interfere with the objective lens 1 even when the stage 2 is displaced.

In the heat-retention box 16, a glass bottom dish 14 is disposed. A hole 14a is formed on a bottom surface of the glass bottom dish 14. To the bottom surface of the glass bottom dish 14, a cover glass 13 on which the cultured cell 12 is disposed is attached. Here, the cover glass 13 is arranged so that the cultured cell 12 on the cover glass 13 attached to the glass bottom dish 14 is located inside the hole 14a.

Further, in a bottom wall of the heat-retention box 16 and above the bottom plate 18, a heater 17 formed from a heating coil is disposed. The heater 17 serves to heat the cultured cell 12 via the glass bottom dish 14.

The heat-retention box 16 has a window 15 which serves to cover an upper opening. The window 15 is formed from a transparent material which would transmit the transmissive lighting beam.

At the bottom of the heat-retention box 16, the objective lens 1 is disposed through the transmission hole 20. The objective lens 1 includes a top lens 1a which is inserted into the transmission hole 20 as to allow for a focusing onto the cultured cell 12. The objective lens 1 has a heater 22 with a sheet-like electrically-heated wire wound around an outer periphery thereof as a heating unit. The heater 22 serves to heat the objective lens 1 with the electrically-heated wire which receives electric currents supplied through a cable 23 and generates heat.

The heaters 22 and 17 are connected to a temperature controller 25 which serves as a temperature controlling unit through cables 23 and 24, respectively.

In the heat-retention box 16, a gas temperature sensor 56a is disposed. The gas temperature sensor 56a serves to detect a gas temperature inside a cell culture space 21 which is a space with a high humidity that serves for the incubation of the sample. A cell temperature sensor 56b is disposed in the glass bottom dish 14. The cell temperature sensor 56b serves to detect the temperature of the cultured cell 12. Further, in the tip portion of the objective lens 1, an objective temperature sensor 56c is disposed. The objective temperature sensor 56c serves to detect the temperature of the tip portion of the objective lens 1.

The gas temperature sensor 56a, the cell temperature sensor 56b, and the objective temperature sensor 56c are connected to the temperature controller 25 via cables 57a, 57b, and 57c, respectively.

The temperature controller 25 controls the temperature of the cultured cell 12 and the objective lens 1 to a respective predetermined temperature, by turning the heaters 17 and 22 ON and OFF based on temperature information provided by the gas temperature sensor 56a, the cell temperature sensor 56b, and the objective temperature sensor 56c.

A plurality of bathes 19 is disposed in the heat-retention box 16 around the glass bottom dish 14. The bathes 19 are filled with humidifying water 19a of a predetermined temperature. The humidifying water 19a evaporates to a moderate degree to keep relative humidity of the cell culture space 21 of the heat-retention box 16 at 100%, in other words, to keep the cell culture space 21 a highly humid space, thereby suppressing evaporation of culture solution 14b in the glass bottom dish 14.

Further, a tube 26 penetrates a side wall of the heat-retention box 16. The tube 26 is connected to a $CO_2$ container 27 so as to supply $CO_2$ gas from the $CO_2$ container 27 to the cell culture space 21. Thus, the $CO_2$ concentration of the cell culture space 21 is maintained, for example, at approximately 5%, and pH value of the cultured cell 12 is maintained, for example, at approximately 7.2 to 7.4.

In the cell incubator 3 with the above-described structure, temperature information from the gas temperature sensor 56a, the cell temperature sensor 56b, and the objective temperature sensor 56c are supplied to the temperature controller 25. The temperature controller 25 turns the heaters 17 and 22 ON and OFF based on the temperature information. The temperature controller 25 controls the heater 22 so that, in particular, a surface temperature and an internal temperature of the objective lens 1 are higher than a dew-point temperature, and lower than a thermal death point of the cultured cell 12.

Specifically, the temperature controller 25 controls the heater 17 so that the temperature of the cultured cell 12 is 37° C., whereas the temperature controller 25 controls the heater 22 so that the temperature of the tip portion of the objective lens 1 is in a range of 1 to 39° C. When thermal resistance between the cultured cell 12 and the objective lens 1 is relatively small, as in the case where an oil immersion objective lens or a water immersion objective lens is employed, the temperature controller 25 controls the temperatures of the tip portion of the objective lens 1, the cultured cell 12, and gas temperature in the cell culture space 21 to 37.05° C., 37° C., and 36.95° C., respectively. Further, when the thermal resistance between the cultured cell 21 and the objective lens 1 is relatively large as in the case where a dry objective lens is employed, the temperature controller 25 controls the temperatures of the tip portion of the objective lens 1, the cultured cell 12, and the gas temperature of the cell culture space 21 to approximately 38° C., 37° C., and 36° C., respectively.

Thus, when the temperature of the objective lens 1 is constantly maintained at a temperature higher than the gas temperature of the cell culture space 21 which is a high humidity space, and higher than the dew-point temperature, dew condensation inside the objective lens 1 can be surely prevented even when the gas in the cell culture space 21 invades into the side of the objective lens 1, whereby the degradation of a microscopic image can be surely prevented from being incurred by the dew condensation inside the objective lens 1. Specifically, when the temperature of the objective lens 1 is set to be constantly higher than the gas temperature of the cell culture space 21 by approximately 0.1° C. to 2° C., the invasion of the gas in the cell culture space 21 of 100% humidity into the objective lens 1 does not cause dew condensation, whereby the degradation in the microscopic image can be prevented.

Further, since the temperature of the objective lens 1 is higher than the gas temperature of the cell culture space 21 only by approximately 0.1° C. to 2° C., the temperature of the cultured cell 12 does not rise excessively, whereby the death of the cultured cell 12 can be prevented and the activity of the cultured cell 12 can be stably maintained.

For example, when the temperature of the objective lens 1 is set higher than the gas temperature of the cell culture space 21 by 1° C., even when the gas in the cell culture space 21 of 100% humidity invades into the objective lens 1, humidity inside the objective lens 1 can be lowered down to approximately 95%, whereby the dew condensation can be prevented.

Further, even when the objective lens 1 is moved upwards from the lower position closer to the cultured cell 12 for focusing thereon, since the temperature of the objective lens 1 is higher than the temperature of the cell culture space 21, dew is not condensed on an outer surface of the top lens 1a. Hence, a clear microscopic image can be obtained without quality degradation by dew condensation.

Next, a second embodiment of the present invention will be described.

Figure 3:
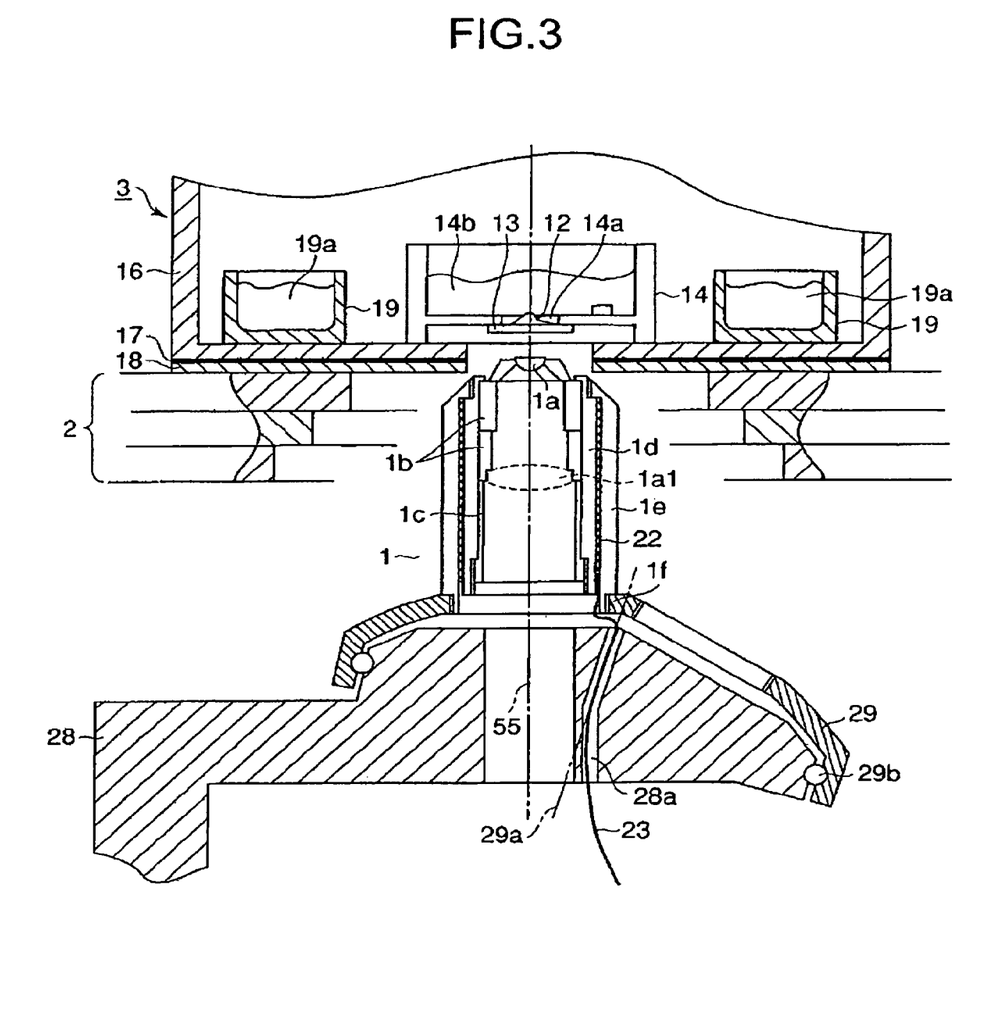
FIG. 3 is a schematic diagram of a structure of main parts of an inverted microscope according to a second embodiment of the present invention.

FIG. 3 shows a schematic structure of main parts of a microscope according to the second embodiment of the present invention, and the same reference characters are assigned to the same elements shown in FIGS. 1 and 2.

Here, the objective lens 1 has the top lens 1a and a group of other lenses 1a1 adhesively fixed to an opening of a cylindrical inner frame 1b. The inner frame 1b is fit into a void in a cylindrical middle frame 1d and secured by a holding tube 1c. On an outer periphery of the middle frame 1d, the sheet-like heater 22 having an electrically-heated coil is adhesively fixed. An outer periphery of the heater 22 is covered by an outer frame 1e which is screwed into the middle frame 1d and secured.

The objective lens 1 with the above-described structure is detachably fixed to the revolver 29 via a threaded portion 1f provided at a lower portion of the outer frame 1e.

On the other hand, the revolver 29 is held by the objective lens holder 28 and rotatable around a rotation axis 29a via a ball 29b. Through the rotation of the revolver 29, one desired objective lens 1 is selectively arranged on the optical axis 55 so as to face the cultured cell 12.

Inside the objective lens holder 28, a penetration hole 28a is formed as an inner axial space along the rotation axis 29a in the vicinity of the rotation axis 29a. The cable 23 serves to supply electric currents to the electrically-heated coil of the heater 22, and passes from the heater 22 through the threaded portion 1f of the revolver 29, and then the penetration hole 28a of the objective lens holder 28, to be connected to the temperature controller 25.

Since the sheet-like heater 22 is incorporated inside the objective lens 1, heat can be surely transferred to the objective lens 1, whereby the subtle temperature control can be realized in terms of space and time.

The cable 23 of the heater 22 further passes through the penetration hole 28a formed along the rotation axis 29a in the vicinity of the rotation axis 29a of the revolver 29 of the objective lens holder 28. Hence, even if the revolver 29 rotates, the range of rotation of the cable 23 can be minimized as to prevent the cable 23 from tangling with the revolver 29, and the rotation of the revolver 29 can be readily realized.

Further, at the focusing, even if the cable 23 moves upwards and downwards together with the objective lens 1, since the cable 23 can sag inside the penetration hole 28a of the objective lens holder 28 to absorb such movement, the cable 23 does not get held.

Still further, since the heater 22 of the objective lens 1 is in contact with the metal inner frame 1b, the holding tube 1c, the middle frame 1d, and the outer frame 1e, the efficiency of thermal conductivity is high and the time constant can be shortened. Therefore the subtle temperature control can be realized in terms of time and space. Thus, unnecessary heating of the cultured cell 12 can be prevented, and the activity of the cultured cell 12 can be readily maintained.

Here in the second embodiment, the objective lens 1 incorporates the sheet-like heater 22 with the electrically-heated coil, so as to allow the supply of electric currents to the heater 22 through the cable 23. However, the same function can be realized with a flow path through which a fluid that is heated outside is supplied to the objective lens 1. Then, the tube which supplies the fluid replaces the cable 23 and passes inside the objective lens holder 28.

Next, a first modification of the second embodiment of the present invention will be described with reference to FIG. 4.

In the first modification of the second embodiment, the revolver 29 as described according to the second embodiment is eliminated. Instead, the objective lens 1 is directly screwed onto the objective lens holder 28 and secured. Characteristic elements alone of the first modification will be described below.

The structure of the objective lens 1 and the heater 22 are the same with those as shown in FIG. 3. There is only one objective lens 1 and which is screwed onto the objective lens holder 28 through the threaded portion if of the outer frame 1e and secured. Further, the cable 23 of the heater 22, without the revolver 29 interposed, extends from the threaded portion if, passes through a penetration hole 28b which serves as an inner space formed inside the objective lens holder 28 and is connected to the temperature controller 25.

Here, the objective lens holder 28 has on a side surface thereof a work hole 28c which serves as a space open to outside, and the work hole 28c communicate the penetrating hole 28b with outside. Further, in the middle of the cable 23, a connector 57 is provided to serve as an electrical contact with which the cable 23 can be divided or reconnected. Attachment/detachment to/from the connector 57 allows for connection to or detachment from the temperature controller 25 of the cable 23. Further, the connector 57 is arranged in the vicinity of a portion where the penetration hole 28b and the work hole 28c are connected, and can be manipulated through the work hole 28c.

According to the second embodiment described above, when the objective lens 1 is screwed onto the revolver 29, the cable 23 of the heater 22 rotates accordingly, incurring the possibility of entanglement of the cable 23. However, in the first modification of the second embodiment, the cable 23 is formed as to be dividable and reconnectable via the connector 57 in the middle. The objective lens is screwed onto the objective lens holder 28 and secured while the connector 57 is detached, and then the connector 57 is connected through manual manipulation from the work hole 28c of the objective lens holder 28, whereby the entanglement of the cable 23 can be prevented. In addition, since the sag of the cable 23 can be adjusted by the manipulation through the work hole 28c, the cable 23 does not erroneously enter the optical path provided for the observation of the cultured cell 12 whereby the degradation of the microscopic image can be prevented.

Here, in the first modification, the entanglement of the cable 23 is prevented through the attachment/detachment of the cable 23 with the connector 57. Alternatively, the same function can be realized with a slidable electrical contact provided in the cable 23.

Next, a second modification of the second embodiment of the present invention will be described in detail with reference to FIG. 5.

In the second modification, the heater 22 described according to the first modification of the second embodiment is eliminated. Instead, a transparent heater is directly disposed on a surface of the lens. Characteristic elements only of the second modification will be described below.

Here, in the objective lens 1, the top lens 1a is adhesively fixed in the opening of the inner frame 1b and an outer surface and an inner surface thereof are coated with a transparent heater 59 which includes a transparent conductive film as a heating member. Since the transparent heater 59 is disclosed also in the Japanese Patent Application Laid-Open No. 2004-141143, detailed description will not be provided here. The transparent heater 59 also has an optical homogeneity to a degree as to prevent degradation of imaging performance of the objective lens 1.

The cable 23 which supplies electric currents to the transparent heater 59 passes through a penetration hole 1b1 provided to the inner frame 1b of the objective lens 1 and a penetration hole 1d1 provided to the middle frame id, further through a gap between the middle frame id and the outer frame 1e, and is guided to the penetration hole 28b of the objective lens holder 28 as to be connected to the temperature controller 25.

With such structure, through the control of the transparent heater 59 in place of the heater 22 described according to the first modification, prevention of dew condensation on the objective lens can be expected to be realized similarly to the second embodiment.

Since the transparent heater 59 is directly applied and arranged to the surface of the top lens 1a of the objective lens 1, the surface of the top lens 1a, the prevention of dew condensation on which is most desired, can be directly heated, and a heating amount to realize a necessary temperature (37.1 to 39° C., for example) can be minimized. Hence, the temperature rise of the cultured cell 12 which is induced by the heating of the objective lens 1 can also be minimized as to prevent degradation of activity of the cultured cell 12.

Figure 4:
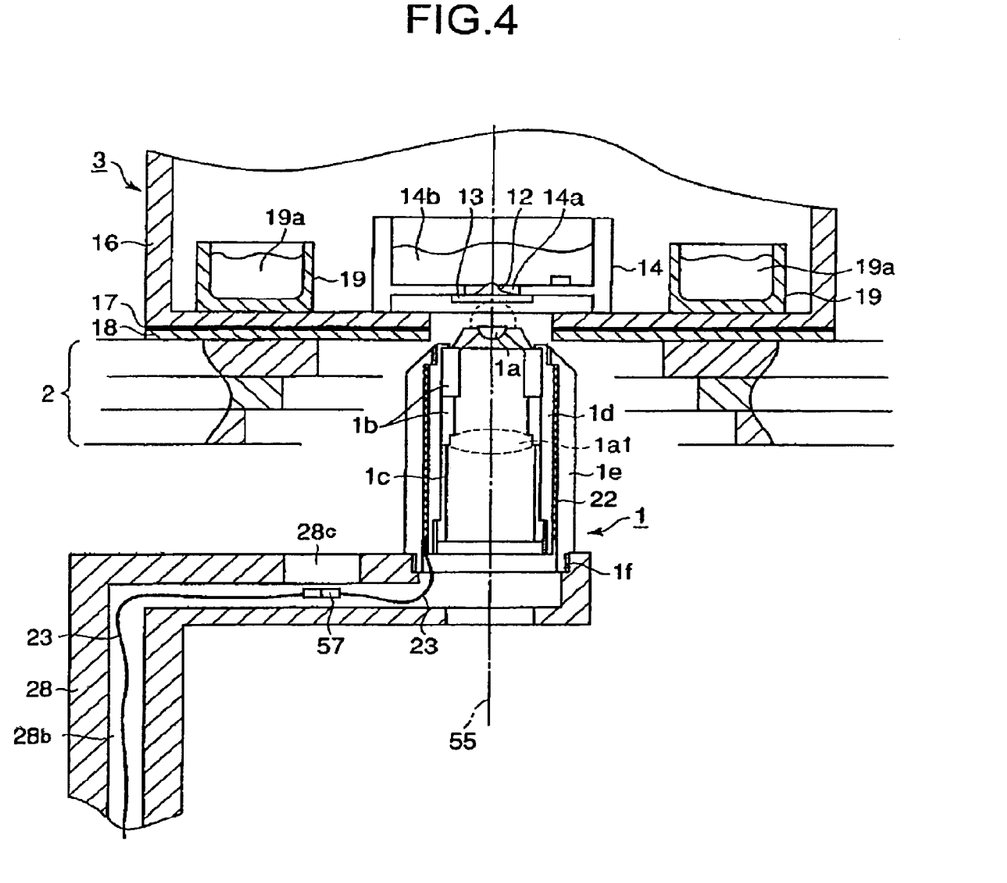
FIG. 4 is a schematic diagram of a structure of main parts of an inverted microscope according to a first modification of the second embodiment.
Figure 5:
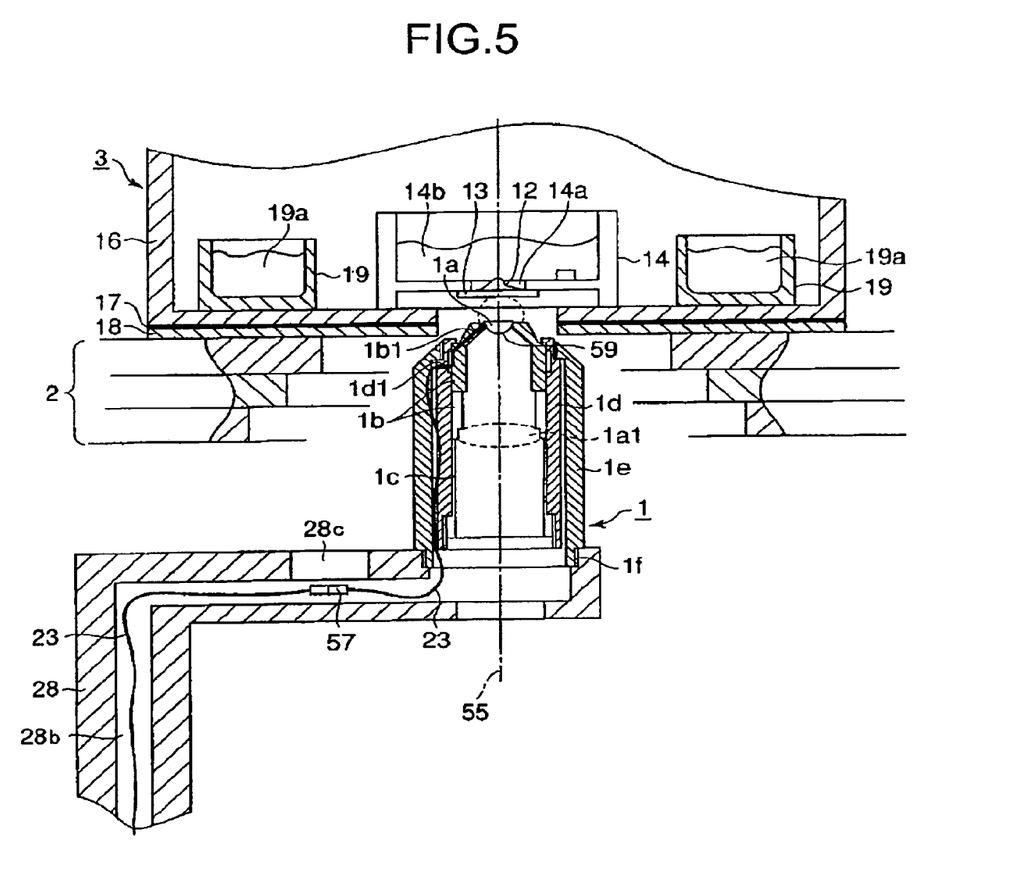
FIG. 5 is a schematic diagram of a structure of main parts of an inverted microscope according to a second modification of the second embodiment.

Here, in the first and the second modifications of the second embodiment described above, when the objective lens 1 is an immersion objective lens, a drop of predetermined oil or water may be applied to an upper portion of the top lens 1a of the objective lens 1 as shown by a broken line in FIGS. 4 and 5, so as to fill a gap between the top lens 1a and the cover glass 13. Then, dew condensation on the inner surface or the like of the top lens 1a inside the objective lens 1 can be prevented by the heater 22 or the transparent heater 59 as described above.

Next, a third embodiment of the present invention will be described.

In the first and the second embodiments described above, the objective lens 1 in the cell incubator 3 disposed on the stage 2 of the inverted microscope is heated in order to achieve prevention of dew condensation on the objective lens 1. In a microscope with a cell incubator according to the third embodiment, substantially the entire microscope including the objective lens can be heated.

Figure 6:
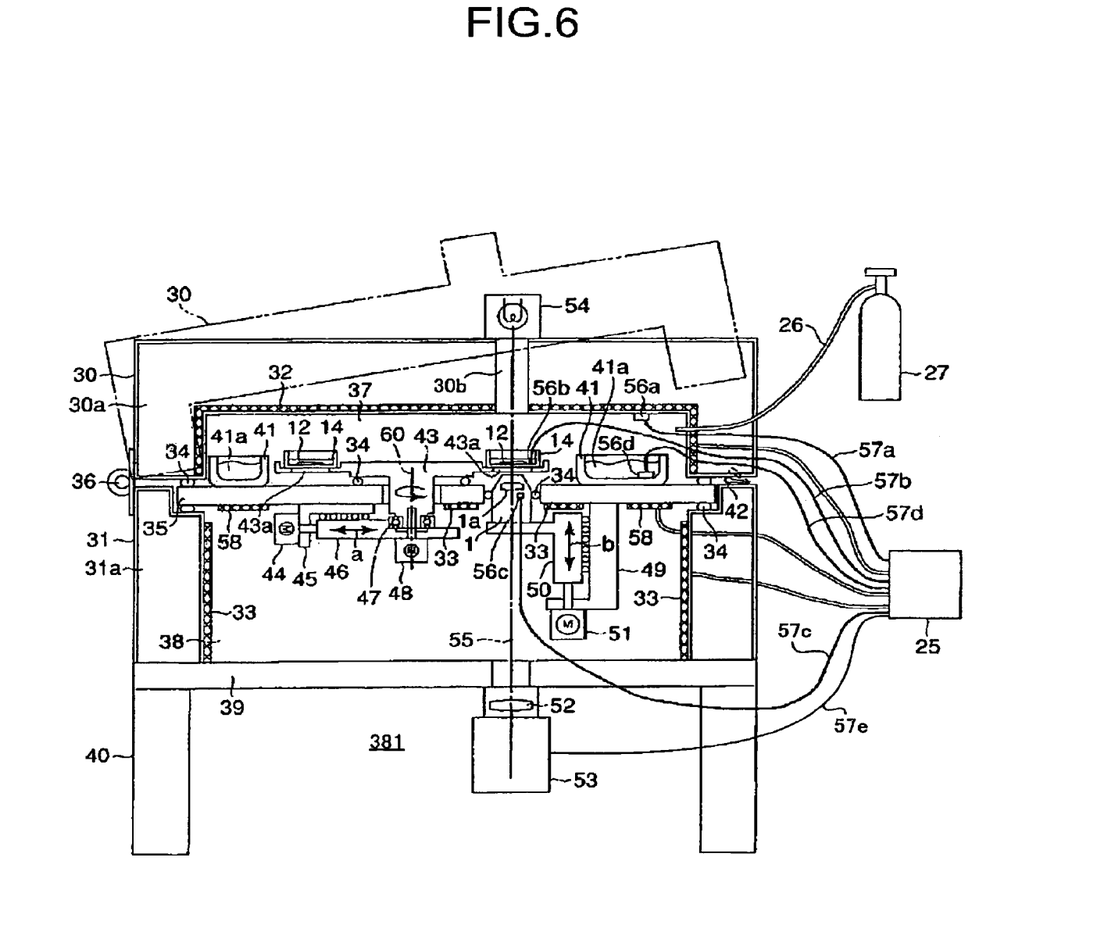
FIG. 6 is a schematic diagram of a structure of main parts of an inverted microscope according to a third embodiment of the present invention.

FIG. 6 shows a schematic structure of main parts of a microscope with a cell incubator according to the third embodiment. The same reference characters are assigned to the same elements as shown in FIG. 2. Here, the microscope with the cell incubator generally has three spaces, i.e.:

(a) a cell culture space 37 which temperature, humidity and $CO_2$ concentration are controlled;

(b) an observation space 38 of the microscope including the objective lens 1 in which only temperature is controlled;

(c) a space 381 provided with an imaging lens 52, a charge coupled device (CCD) 53, and a light source 54 for transmissive lighting which is the same space with outside and which temperature, humidity, and $CO_2$ are not controlled.

The cell culture space 37 listed above as (a) which is a high humidity space is covered with a cover box 30, which serves as an opening/closing unit and is provided with a space 30a inside for thermal insulation. On an inner wall of the cover box 30, a heater 32 is provided to heat the cell culture space 37. The cover box 30 is provided with a hinge 36 so that the cover box 30 can be opened/closed with rotation around the hinge 36. Thus, the cultured cell 12 can be taken in and out from the cell culture space 37. When the cover box 30 is opened, the cell culture space 37 communicates with the space 381 which is the outside space. A chain double-dashed line shown in FIG. 6 indicates a state of the open cover box 30. A switch 42 is provided as an open/close detecting unit to detect the open/close state of the cover box 30 in accordance with the opening/closing of the cover box 30. The state of the switch 42, in other words, the open/close state of the cover box 30 is monitored by the temperature controller 25.

In the cell culture space 37, a plurality of bathes 41 is disposed similarly to the first embodiment described above. The bathes 41 are filled with humidifying water 41a to humidify the cell culture space 37. A tube 26 penetrates a side wall of the cover box 30. The tube 26 is connected to the $CO_2$ container 27 so as to supply $CO_2$ gas in the $CO_2$ container 27 to the cell culture space 37 as to maintain pH of the cultured cell 12 at a constant level.

Here, the cell culture space 37 is divided by an observation space 38 and a divider 35. The divider 35 is sealed with a sealing member 34 such as an O ring as to prevent leakage of water vapor, $CO_2$, or the like into the observation space 38 from the cell culture space 37.

The cell culture space 37 is provided with the gas temperature sensor 56a. The gas temperature sensor 56a serves to detect a gas temperature of the cell culture space 37. The glass bottom dish 14 is provided with the cell temperature sensor 56b. The cell temperature sensor 56b serves to detect a temperature of the cultured cell 12. On the tip portion of the objective lens 1, the objective temperature sensor 56c is provided. The objective temperature sensor 56c serves to detect a temperature of the top lens 1a. In the humidifying water 41a of the bath 41, a humidifying water temperature sensor 56d is provided. The humidifying water temperature sensor 56d serves to detect a temperature of the humidifying water 41a. The gas temperature sensor 56a, the cell temperature sensor 56b, the objective temperature sensor 56c, and the humidifying water temperature sensor 56d are connected to the temperature controller 25 via cables 57a, 57b, 57c, and 57d, respectively.

The temperature controller 25 controls temperatures of respective elements by turning the heater 32 and other heaters mentioned later ON and OFF based on temperature information provided from the gas temperature sensor 56a, the cell temperature sensor 56b, the objective temperature sensor 56c, and the humidifying water temperature sensor 56d.

On an upper portion of the cover box 30, the light source 54 is provided for lighting at observation of the cultured cell 12. Light from the light source 54 passes through a hole 30b provided in the cover box 30 and serves to illuminate the cultured cell 12 on the optical axis 55.

In the cell culture space 37, plural glass bottom dishes 14 are disposed, to each of which a cover glass (not shown) is attached. The cultured cell 12 is attached to the cover glass. The glass bottom dishes 14 are placed in plural holes 43a (two in the drawing), respectively, provided on the stage 43 and are movable along a plane which is vertical to the optical axis 55.

A stage 43 hangs from the divider 35 and is supported thereby. The stage 43 is rotatable around a rotation axis 60 (direction of rotation is referred to as θ direction hereinbelow) and linearly movable along a direction of an arrow a which is a horizontal direction (hereinbelow referred to as R direction), and realizes a movement along two polar coordinate of the θ direction and the R direction.

More specifically, an L-shaped fixed guide 45 is fixed to the divider 35. The fixed guide 45 supports a movable guide 46 and an R motor 44 which serves to move the movable guide 46 in the R direction is fixed. Thus, the movable guide 46 is movable along the R direction by the R motor 44. The movable guide 46 holds the stage 43 via a bearing 47 in a rotatable manner. A θ motor 48 provided to the movable guide 46 is connected to the rotation axis of the stage 43 and realizes rotation of the stage 43.

On the other hand, the divider 35 has a fixed guide 49 disposed in the vertical direction. The fixed guide 49 has a movable guide 50 which is movable in a vertical direction shown by an arrow b (z direction) in the drawing. The objective lens 1 is attached to the movable guide 50, and further a Z motor 51 is connected to the movable guide 50. The Z motor 51 serves to move the movable guide 50 in the direction shown by the arrow b (z direction), and along with the movement of the movable guide 50 resulted therefrom, the objective lens 1 moves in the vertical direction. According to the movement of the objective lens 1, the relative distance between the objective lens 1 and the stage 43 changes to allow for the focusing of the objective lens 1 on the cultured cell 12. In other words, the fixed guide 49, the movable guide 50, and the Z motor 51 function as a focusing mechanism for the objective lens 1.

Here, the gap between the stage 43 and the divider 35, and the gap between the objective lens 1 and the divider 35 are slidably sealed by the sealing members 34 such as an O ring in order to prevent leakage of water vapor or $CO_2$ from the cell culture space 37 into the observation space 38.

The observation space 38 which is a sealed space divided by the sealing member 34 from the cell culture space 37 is surrounded by a bottom box 31 in which the space 31a for thermal insulation is provided. In the observation space 38, a driving unit of the stage 43, the focusing mechanism of the objective lens 1, or the like mentioned above are arranged together with the main body of the microscope except the tip portion of the objective lens 1.

On an inner side wall of the bottom box 31, the heater 33 is provided similarly to the cover box 30, and similarly on a lower surface of the divider 35, the heater 33 is provided in the vicinity of the objective lens 1. The heater 33 is a heating unit to heat the objective lens 1 and serves to heat the objective lens 1 and the focusing mechanism up to a temperature equal to the temperature of the observation space 38.

Here, as mentioned above, the heater 33 is turned ON and OFF by the temperature controller 25 to control the temperature based on the temperature information provided from the objective temperature sensor 56c disposed at the tip portion of the objective lens 1.

On the bottom surface of the divider 35 located inside the observation space 38, another heater 58 is provided in the vicinity of the humidifying water 41a. The heater 58 is controlled by the temperature controller 25 based on the temperature information provided from the humidifying water temperature sensor 56d described above, and serves to maintain the temperature of the humidifying water 41a at a constant level. The heater 58 is controlled via a different system from the system controlling the heater 33.

Below the bottom surface of the observation space 38, a base 39 is disposed. To the base 39, a leg 40 is attached. The leg 40 supports the entire microscope with the cell incubator together with the base 39 and the bottom box 31.

On a bottom surface of the base 39, the imaging lens 52 and the CCD camera 53 are disposed on the optical axis 55 of the objective lens 1 as an image pick-up unit. The imaging lens 52 serves to form an observation image, which is an optical image of the cultured cell 12 infinitely projected by the objective lens 1, on an imaging surface of the CCD camera 53. The CCD camera 53 generates the observation image by picking up the observation image formed on the imaging surface. The observation image generated by the CCD camera 53 is supplied to the temperature controller 25 as an output via a cable 57e and subjected to image processing.

A manner of microscopic observation with such structure will be described below.

First, the cover box 30 is opened, and the glass bottom dish 14 in which the cultured cell 12 is disposed is placed in the predetermined hole 43a of the stage 43. Then, the cover box 30 is closed.

The light source 54 is turned on via a manipulation of a microscope controller (not shown). With the driving of the R motor 44 and the θ motor 48, the stage 43 is moved in the θ direction and the R direction, so that a portion of the cultured cell 12 whose observation is desired is moved onto the optical axis 55. Then the microscope controller (not shown) drives the Z motor 51 to move the objective lens 1 in the Z direction to focus the objective lens 1 on the cultured cell 12.

The alignment of the portion of the cultured cell 12 which observation is desired and the focusing of the objective lens 1 are performed while the observer looks at the observation image which is a live image picked up by the CCD camera 53 controlled by the microscopic controller (not shown).

Thus after the setting of plural portions to be observed and the focusing positions by the microscope controller (not shown), and further after the setting of an interval of the observation time, with a push-down of a start button or the like (not shown) at a predetermined set observation time, the CCD camera 53 picks up a static image to allow for automatic observation of a time course of the cultured cell 12. Here, the light source 54 is turned on only at the observation of the live image and the image pick-up by the CCD camera 53 to capture the time course.

When the observation of the time course of the cell takes a long time period, e.g., a time period equal to or longer than three days, the cover box 30 is opened for taking-out of the cultured cell 12 and the exchange of a culture media as appropriate.

Next, the environment for cell culture and the temperature control of the microscope will be described.

First, the $CO_2$ concentration is controlled by a $CO_2$ sensor (not shown) and a controller (not shown). Specifically, an electromagnetic valve or the like of the $CO_2$ container 27 is turned ON/OFF, to render the $CO_2$ concentration in the cell culture space 37 to, for example, 5%. Thus, the pH of the culture media in which the cultured cell 12 is immersed can be maintained approximately at 7.2 to 7.4, whereby an activity of the cell can be maintained.

The temperature controller 25 controls the temperatures of respective elements at a constant level by turning ON and OFF the heaters 32, 33, and 58 based on the temperature information provided from the gas temperature sensor 56a, the cell temperature sensor 56b, the objective temperature sensor 56c, and the humidifying water temperature sensor 56d. The temperature controller 25 controls the heater 33, in particular, so that the surface temperature and the internal temperature of the objective lens 1 are at a level higher than the dew-point temperature and lower than the thermal death point of the cultured cell 12.

Specifically, the temperature controller 25 controls so that the temperature of the observation space in which the objective lens 1 is placed, the temperature of the cultured cell 12, the gas temperature of the cell culture space 37, and the temperature of the humidifying water 41a are 37° C., 37° C., 37° C., and 35 to 36.9° C., respectively.

Thus, since the temperature of the objective lens 1 is set higher than the temperature of the humidifying water 41a approximately by 0.1° C. to 2° C., invasion of the gas from the cell culture space 21 into the objective lens 1 does not cause dew condensation, whereby the degradation of the microscopic image can be prevented. Further, when the temperature of the objective lens 1 is higher than the gas temperature of the humidifying water 41a by 1° C., even when the vapor of the humidifying water 41a invades into the objective lens 1, the humidity can be lowered down approximately to 95%, whereby the dew condensation does not occur.

In the third embodiment, the cell culture space 37 and the observation space 38 are maintained at the same temperature, i.e., 37° C. Hence, the temperature of the cell culture space 37 is similarly higher than the temperature of the humidifying water 41a approximately by 1° C. to 2° C., and the differential temperature renders the relative humidity of the cell culture space 37 approximately 90 to 99%. Thus, the evaporation from the culture media of the cultured cell 12 can be suppressed. When less change in osmolality in and out the cultured cell 12 is preferable, the humidifying water 41a may be maintained at a relatively higher temperature, e.g., 36.9° C. Then, the relative humidity of the cell culture space 37 is approximately 99%, and the evaporation from the culture media can be suppressed and the activity of the cell can be readily maintained.

On the other hand, if the prevention of dew condensation in the cell culture space 37 is prioritized, the temperature of the humidifying water 41a may be set, for example, at 35° C. Then, the relative humidity of the cell culture space 37 is approximately 90%, and even if the variation in temperature inside the cell culture space 37 produces a portion with a low temperature, as far as the low temperature is equal to or lower than 35° C., dew condensation would not happen. Thus, the temperature control of the cell culture space 37 can be readily achieved.

A portion around the sealing member 34, for example, tends to lose heat through transfer to outside air. When the temperature of the humidifying water 41a is set slightly lower, however, the dew condensation can be prevented. Hence, the temperature of the humidifying water 41a is changed in the range of 35 to 36.9° C., i.e., in the range of 90 to 99% humidity of the cell culture space 37, depending on the supersensitivity of change in osmolality of the cell and likelihood of dew condensation in the cell culture space 37.

Dissimilar to the first embodiment, substantially the entire microscope is heated and maintained in a heated state while the observation space 38 in which the objective lens 1 is placed and the cell culture space 37 are kept in the same temperature, i.e., 37° C. Hence there is little temperature variation in the objective lens 1, which means less likelihood of dew condensation. Further, since the temperature of the humidifying water 41a can be set slightly higher, the evaporation from the culture media can be suppressed and the activity of the cell can be readily maintained, as mentioned above.

Further, even when the objective lens 1 is moved upwards from the lower position as to approach the cultured cell 12 for focusing, since the temperature of the objective lens 1 and the temperature of the cell culture space 37 are the same, dew condensation does not occur on the outer surface of the top lens 1a of the objective lens 1, whereby a clear microscopic image can be obtained without degradation of image quality by the dew condensation.

Still further, since the objective lens 1 and the focusing mechanism are maintained in a constant temperature equal to the temperature of the observation space 38, the thermal expansion of the focusing mechanism and the temperature change of the objective lens 1 do not render the image out of focus.

Maintenance of a sharp temperature difference in a small space, e.g., a space between the tip portion of the objective lens 1 and the cultured cell 12 as in the first embodiment is difficult to control. In the third embodiment, however, since the objective lens 1, the cultured cell 12, and the cell culture space 37 are maintained at the same temperature, the control is easy. Thus, along with the prevention of dew condensation in the objective lens 1, the cultured cell 12 can be maintained at 37° C. as to maintain a favorable activity state of the cell.

Here, the light source 54 and the CCD camera 53 are disposed in a same space with outside air, i.e., space outside the space where temperature is controlled. The light source 54 is disposed in the outside space to prevent a negative influence of the heat generation thereof on the cell culture space 37. On the other hand, since the CCD camera 53 easily generates noise when the temperature rises, the CCD camera 53 is disposed in the outside space which usually has a temperature lower than 37° C. Here, though the imaging lens 52 is disposed in the outside space, since the imaging lens 52 does not suffer from negative influence of defocusing caused by the temperature change as much as the objective lens 1 does, no major inconvenience arises. Of course, the imaging lens 52 can be disposed in the observation space 38 maintained at a constant temperature.

Taking-in and out of the cultured cell 12 from the cell culture space 37 for the exchange of culture media will be described.

In the third embodiment, substantially the entire microscope is heated and maintained in a heated-state. Hence, dew condensation would not occur inside the objective lens 1. However, when the cover box 30 is opened for the exchange of the culture media or the like, an outside air of a usually lower temperature than 37° C. may flow into the cell culture space 37 as to cool down the objective lens 1. Since the objective lens 1 is normally maintained at 37° C., dew condensation does not occur on the surface thereof. However, since the inside of the objective lens 1, though with suppressed humidity, still has a humidity of approximately 90%, sudden exposure to the cool outside air may induce a sharp temperature drop to cause dew condensation inside the objective lens 1.

To prevent such inconvenience, the temperature controller 25 detects opening/closing of the cover box 30 via the switch 42. When the cover box 30 is open, the temperature controller 25 sets an output of the heater 33 to a higher level than a normal level in response to an output from the switch 42, thus controlling the heater 33 as to heat up more rapidly than when the cover box 30 is closed and to offset the rapid cooling of the objective lens 1, whereby the objective lens 1 is maintained at 37° C. to prevent dew condensation.

When the cover box 30 is open for a long time period, even after the cover box 30 is closed, it takes some time until the temperature inside recovers to a former temperature, i.e., 37° C. Hence, the temperature controller 25 monitors the length of time period during which the cover box 30 is open based on the output from the switch 42. Depending on the time length when the cover box 30 is open, the temperature controller 25 changes a time length during which the heater 33 provides a higher output than a normal output, and makes the heater 33 heat slightly longer after the cover box 30 is closed. In other words, the temperature controller 25 detects an open time when the cover box 30 is in the open state via the switch 42, and when the closed state of the cover box 30 is detected via the switch 42, the temperature controller 25 controls the heater 33 as to continue heating at a higher speed than when the cover box 30 is in the closed state for a predetermined time period after the time of detection depending on the length of open time until the detection of the closed state.

Though such function may be realized similarly by the detection of temperature drop by the objective temperature sensor 56c, the temperature sensor tends to fail to follow a sharp temperature change. Hence, the monitoring with the switch 42 is more preferable and allows for swift prevention of temperature drop of the objective lens 1 and dew condensation.

If the cover box 30 is maintained in the open state for excessively long time period, heat suddenly generated by the heater 33 is transferred to the cultured cell 12 after the closing of the cover box 30, thereby rendering the temperature of the cultured cell 12 higher than 37° C. To prevent such inconvenience, if the cover box 30 is maintained in the open state for a longer time period than a predetermined time period, while the output of the heater 33 is made higher than a normal level, the stage 43 is rotated, and the cultured cell 12 is retrieved outside the observation range off the optical axis 55 of the objective lens 1. After the objective temperature sensor 56c starts to stably indicate 37° C., the cultured cell 12 is returned onto the optical axis 55. Such coordination is controlled by the microscope controller (not shown) mentioned above and the temperature controller 25.

When the switch 42 does not work properly due to some defects, or when the temperature of the outside is excessively low to cause rapid cooling of the objective lens 1, resulting in dew condensation inside the objective lens 1, the degradation of the microscopic image caused by dew condensation is detected by the CCD camera 53, and the heater 33 performs heating with an even larger output than the large output for the dew condensation prevention described above which is larger than the normal output, whereby the dew condensation is eliminated. More particularly, the temperature controller 25 performs processing on the observation image generated by the CCD camera 53 as to determine whether the dew condensation occurs on the surface or inside the objective lens 1. On determining that dew condensation occurs, the temperature controller 25 controls the heater 33 as to perform more rapid heating than on determining that dew condensation does not occur. When it is confirmed that dew condensation is eliminated via the detection with the CCD camera 53, the temperature controller 25 reduces the amount of heating and returns the control back to normal, i.e., the control performed when the cover box 30 is closed. Here, the cultured cell 12 may be retrieved for the prevention of over heating similarly as described above.

Thus, the temperature of the objective lens 1 becomes higher than the temperature of the humidifying water 41a, the water vapor invading into the objective lens 1 does not saturate, in other words, the dew condensation can be securely prevented, whereby the degradation in the microscopic image caused by dew condensation inside the objective lens 1 can be surely prevented. More specifically, when the temperature of the objective lens 1 is set higher than the temperature of the humidifying water 41a by 0.1 to 2° C., dew condensation inside the objective lens 1 can be prevented. Further, the excessive increase in the temperature of the cultured cell 12 can be prevented, and the activity of the cell can be securely maintained.

Further, since the temperature of the objective lens 1 is increased only for a predetermined time period according to the length of the time period during which the cover box 30 is open to let the cell culture space 37 which is a high humidity space and the outside air communicate, the dew condensation inside the objective lens 1 due to the temperature drop of the objective lens 1 can be prevented.

Further, when the cover box 30 remains open for a long time period and increase in output of the heater 33 above the normal output is required, the cultured cell 12 is retrieved out of the optical axis 55 of the objective lens 1 before the increase in the temperature of the objective lens 1. Hence, even when the objective lens 1 is heated, the cultured cell 12 is not heated therewith, whereby damage to the cultured cell 12 can be alleviated.

It should be noted that the present invention is not limited to the embodiments described above, and in practice, various modifications can be realized without change in the gist thereof. For example, in the above-described embodiments, the inverted microscope is described. However, the present invention is also applicable to a non-inverted microscope. Further, the stage 43 may be an XY stage with an orthogonal coordinate rather than the R, θ stage with the polar coordinate. Further, though in the above embodiments only one objective lens is described, plural objective lenses may be provided. Still further, the cell culture environment which is described as having 5% $CO_2$ concentration can be set to a different concentration with a different gas, such as $O_2$, $N_2$, a mixture thereof, depending on the employed cell and culture media. Still further, the container to place the cultured cell 12 in is not limited to the glass bottom dish 14, and a plastic dish, a multiple plate or the like is also applicable.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A microscope comprising:
   a high humidity space that is maintained at a predetermined gas temperature and a predetermined relative humidity for culture of a living sample;
   a first heater that maintains the high humidity space at the predetermined gas temperature;
   a first temperature sensor that detects a temperature of the living sample;
   an objective lens which includes a tip portion with a top lens that is disposed in the high humidity space, and which enables observation of the living sample incubated inside the high humidity space;
   a second heater that heats the objective lens;
   a second temperature sensor that detects a temperature of the tip portion of the objective lens; and
   a temperature controller that controls the first heater and the second heater so that the temperature of the tip portion of the objective lens is higher than a dew-point temperature and lower than a thermal death point of the living sample, based on information detected by the first temperature sensor and the second temperature sensor.

2. The microscope according to claim 1, further comprising:
   a third temperature sensor that detects the gas temperature of the high humidity space;
   wherein the temperature controller controls the second heater so that the temperature of the tip portion of the objective lens is higher than the gas temperature, based on information detected by the second temperature sensor and the third temperature sensor.

3. The microscope according to claim 1, wherein humidifying water at a predetermined water temperature is provided inside the high humidity space to keep the high humidity space at the predetermined relative humidity, and the temperature controller controls the second heater so that the temperature of the tip portion of the objective lens is higher than the predetermined water temperature.

4. The microscope according to claim 3, further comprising a third heater to maintain the predetermined water temperature.

5. The microscope according to claim 1, further comprising:
   an opening/closing unit that opens the high humidity space to an outside space; and
   an open/close detector that detects whether the opening/closing unit is open or closed;
   wherein the temperature controller controls the second heater so that the heater performs a more rapid heating when the opening/closing unit is open than when the opening/closing unit is closed.

6. The microscope according to claim 5, wherein the open/close detector detects an open time during which the opening/closing unit remains open; and
   wherein when the open/close detector detects that the opening/closing unit is closed after being open, the temperature controller controls the second heater to continue the rapid heating for a predetermined time period from a time when the opening/closing unit is detected to be closed, depending on a length of the open time up to the detection of the closed state.

7. The microscope according to claim 6, wherein the high humidity space includes a movable stage which removes the living sample from a range of observation of the objective lens if the opening/closing unit remains open for longer than a predetermined time period.

8. The microscope according to claim 1, further comprising an image pickup unit that picks up an optical image of the living sample formed by the objective lens to generates an observation image;
   wherein the temperature controller determines whether dew condensation occurs at least one of on a surface of and in an interior of the objective lens through processing of the observation image, and controls the second heater to perform a more rapid heating if the temperature controller determines that the dew condensation occurs than if the temperature controller determines that the dew condensation does not occur.

9. The microscope according to claim 1, wherein the objective lens has a main body which, except for the tip portion, is disposed in a sealed space different from the high humidity space, and the second heater is disposed at a position different from a position of the objective lens in the sealed space, and heats the objective lens and the sealed space to a same temperature.

10. The microscope according to claim 9, further comprising a focusing mechanism which is disposed in the sealed space and performs focusing of the objective lens on the living sample;
wherein the second heater heats the objective lens and the focusing mechanism to the same temperature as the sealed space.

11. A microscope comprising:
a high humidity space that is maintained at a predetermined gas temperature and a predetermined relative humidity for culture of a living sample;
a first heater that maintains the high humidity space at the predetermined gas temperature;
a first temperature sensor that detects a temperature of the living sample;
an objective lens which includes a tip portion with a top lens that is disposed in the high humidity space, and which enables observation of the living sample incubated inside the high humidity space;
a second heater that heats the objective lens;
a second temperature sensor that detects a temperature of the tip portion of the objective lens;
an opening/closing unit that opens the high humidity space to an outside space;
an open/close detector that detects whether the opening/closing unit is open or closed; and
a temperature controller that controls the first heater and the second heater so that the temperature of the tip portion of the objective lens is higher than a dew-point temperature and lower than a thermal death point of the living sample, and so that the second heater performs a more rapid heating when the opening/closing unit is open than when the opening/closing unit is closed, based on information detected by the first temperature sensor and the second temperature sensor.

12. The microscope according to claim 11, wherein the temperature controller controls the second heater so that the temperature of the tip portion of the objective lens is higher than the gas temperature.

13. The microscope according to claim 11, wherein humidifying water at a predetermined water temperature is provided inside the high humidity space to keep the high humidity space at the predetermined relative humidity, and the temperature controller controls the second heater so that the temperature of the tip portion of the objective lens is higher than the predetermined water temperature.

14. The microscope according to claim 13, further comprising a third heater to maintain the predetermined water temperature, and a third temperature sensor that detects the water temperature.

15. The microscope according to claim 11, wherein the open/close detector detects an open time during which the opening/closing unit remains open; and
wherein when the open/close detector detects that the opening/closing unit is closed after being open, the temperature controller controls the second heater to continue the rapid heating for a predetermined time period from a time when the opening/closing unit is detected to be closed, depending on a length of the open time up to the detection of the closed state.

16. The microscope according to claim 15, wherein the high humidity space includes a movable stage which removes the living sample from a range of observation of the objective lens if the opening/closing unit remains open for longer than a predetermined time period.

17. A method of heating a microscope, comprising:
detecting a temperature of a living sample in a high humidity space, and controlling a first heater such that a temperature of the living sample in the high humidity space, which is maintained at a predetermined gas temperature and a predetermined relative humidity for culture of the living sample, is lower than a thermal death point of the living sample, based on detected temperature information; and
detecting a temperature of a tip portion of an objective lens of the microscope, and controlling a second heater such that the temperature of the tip portion of the objective lens is higher than a dew-point temperature, based on detected temperature information, wherein the objective lens includes the tip portion with a top lens that is disposed in the high humidity space and enables observation of the living sample incubated inside the high humidity space.

18. The method according to claim 17, wherein the second heater is controlled such that the temperature of the tip portion of the objective lens is higher than the temperature of the living sample by 0.1 to 2° C.

19. The method according to claim 17, wherein the predetermined relative humidity is 90 to 100%, and humidifying water at a predetermined water temperature is provided inside the high humidity space to keep the high humidity space at the predetermined relative humidity; and
wherein the second heater is controlled such that the temperature of the tip portion of the objective lens is higher than the predetermined water temperature by 0.1 to 2° C.

* * * * *